United States Patent [19]
Fish et al.

[11] Patent Number: 5,561,168
[45] Date of Patent: Oct. 1, 1996

[54] IODIDE REMOVAL PROCESS

[75] Inventors: Barry B. Fish, St. Albans; William D. Prince, Charleston; Michael P. Spratt, Scott Depot, all of W. Va.

[73] Assignee: Union Carbide Chemicals & Plastics Technology Corporation, Danbury, Conn.

[21] Appl. No.: 4,543

[22] Filed: Jan. 14, 1993

Related U.S. Application Data

[62] Division of Ser. No. 767,487, Sep. 30, 1991, Pat. No. 5,220,058.

[51] Int. Cl.$^6$ ............... C08F 8/34; B01D 15/04; B01J 39/18; B01J 41/12
[52] U.S. Cl. ............ 521/33; 210/683; 521/30; 525/350; 525/370
[58] Field of Search ............ 521/33, 30; 525/350, 525/370; 210/683

[56] References Cited

U.S. PATENT DOCUMENTS

| | | | |
|---|---|---|---|
| 2,891,916 | 6/1959 | Hwa | 521/33 |
| 3,085,072 | 4/1963 | Zima | 521/33 |
| 3,454,503 | 7/1969 | Blankenhorn | 521/33 |
| 4,615,806 | 10/1986 | Hilton | 210/690 |

FOREIGN PATENT DOCUMENTS

| | | |
|---|---|---|
| 0296584 | 6/1988 | European Pat. Off. . |
| 3329781 | 8/1983 | Germany . |
| 2112394 | 12/1981 | United Kingdom . |

OTHER PUBLICATIONS

F. Helfferich, "Ion Exchange", 168–169 (1962) McGraw–Hill (New York).

*Primary Examiner*—Fred Zitomer
*Attorney, Agent, or Firm*—E. C. Trautlein

[57] ABSTRACT

This invention relates to the use of ion exchange resins having metal-exchanged thiol functional groups in removing iodide impurities from carboxylic acids and/or carboxylic acid anhydrides. More particularly, this invention provides a process for removing iodide impurities from liquid carboxylic acids and/or carboxylic acid anhydrides using ion exchange resins in which thiol functional groups have been exchanged with silver, palladium or mercury.

1 Claim, 5 Drawing Sheets

FIG. 1

□ METHYL IODIDE, 30% EXCHANGE  △ HEXYL IODIDE, 30% EXCHANGE  ◇ METHYL IODIDE, 50% EXCHANGE  × HEXYL IODIDE, 50% EXCHANGE

FIG. 2

× METHYL IODIDE   □ HEXYL IODIDE

IODIDE REMOVAL PROCESS

This application is a division of prior U.S. application Ser. No. 07/767,487 Filing Date Sept. 30, 1991 U.S. Pat. No. 5,220,058.

FIELD OF THE INVENTION

The present invention relates to a process for removing iodide impurities (e.g., hydrogen iodide, alkyl iodides and iodide salts) from carboxylic acids and/or carboxylic acid anhydrides using certain ion exchange resins. In particular, the present invention relates to a process for purifying acetic acid and/or acetic anhydride prepared by the rhodium-catalysed, methyl iodide-promoted carbonylation of methanol and/or methyl acetate using certain metal-exchanged thiol resins.

CROSS REFERENCES TO RELATED APPLICATIONS

Published European Patent Application 296,584 discloses a method for producing silver-exchanged macroreticular resins suitable for removing halides from liquid carboxylic acid contaminated with a halide impurity by contacting the liquid halide-contaminated acid with a silver(1)-exchanged macroreticular resin. The halide reacts with the resin-bound silver and is removed from the carboxylic acid stream. Only resins with silver-exchanged sulfonic functional groups are specifically exemplified. This published European application claims the priority of commonly assigned copending U.S. patent application Ser. No. 65,755, filed Jun. 24, 1988 (now abandoned). Commonly assigned U.S. patent application Ser. No. 552,327, filed Jul. 13, 1990 (now abandoned) is a continuation of the latter application. Commonly assigned U.S. patent application 721,310, filed Jun. 26, 1991, is a continuation of said U.S. patent application 552,327.

DESCRIPTION OF THE RELATED ART

It is known that a problem associated with acetic acid and/or acetic anhydride produced by carbonylation of methanol and/or methyl acetate in the presence of a rhodium/methyl iodide catalyst system is that, even after distillation, the acetic acid and/or acetic anhydride frequently contains small amounts of iodide impurities. While the exact nature of these impurities is not known for certain, they probably comprise a mixture of hydrogen iodide, alkyl iodides and iodide salts. Such impurities are particularly troublesome since they poison many of the catalysts which are employed in subsequent chemical conversions of the acetic acid and/or acetic anhydride. A case in point are the catalysts used to prepare vinyl acetate from ethylene, acetic acid and oxygen-containing gas which are extremely sensitive to iodide impurities.

Several methods of removing iodide impurities from acetic acid and/or acetic anhydride are known. For example, British Patent specification 2,112,394 teaches the use of anion exchange resins for that purpose.

In addition, U.S. Pat. 4,615,806 discloses the removal of iodide impurities from nonaqueous organic media such as acetic acid by the use of a silver or mercury containing macroreticular strong acid cation exchanged resin such as Amberlyst® 15. Only resins with metal-exchanged sulfonic functional groups are specifically exemplified. The silver or mercury is bonded to the resin by an ionic bond. Such resins are subject to deactivation by divalent and trivalent cations such as aluminum and iron that may be present in the acid or anhydride being purified. Further, the silver or mercury in such resins can be lost to some extent when the resins are washed with water containing cation impurities after use to remove the carboxylic acid or anhydride from the resin prior to removal of the spent resin from the bed for metal reclamation. The acid or anhydride in the spent resin is a potential safety hazard. The resins of above-mentioned published European application 296,584 have similar drawbacks.

SUMMARY OF THE INVENTION

It has now been found that ion exchange resins having metal-exchanged thiol functional groups can be used for removing iodide impurities from carboxylic acids and/or carboxylic acid anhydrides. According to the present invention, there is provided a process for removing iodide impurities from liquid carboxylic acid and/or carboxylic acid anhydride using an ion exchange resin in which thiol functional groups have been exchanged with silver, palladium or mercury.

DESCRIPTION OF THE PREFERRED EMBODIMENT

The ion exchange resins used in the process of this invention may be of the gel, mesoporous or macroporous type, but are preferably of the mesoporous or macroporous type. The resins may be cross-linked polyacrylic or polystyrene resins, acrylate resins, phenol-formaldehyde resins, or any other suitable polymeric material that contains thiol functional groups exchanged with silver, palladium or mercury. Prior to exchange with the metal, the resins preferably contain from 0.1 to 2.5 milliequivalents of thiol groups per milliliter of resin. More preferably, the unexchanged resins contain from 1 to 2 milliequivalents of thiol groups per milliliter of resin. Thiol groups are only weakly acidic and the bonds formed between the metals and the thiol groups in the exchanged resins are covalent bonds. Suitable thiol resins can be produced by processes known in the art.

In addition to thiol groups, other functional groups may be present in minor amounts in the resin starting materials used to produce the metal-exchanged resins used in process of the present invention For example, a minor amount (e.g., from 1% to 20%) of the functional groups in resins may be sulfonic acid groups as a result of oxidation of the original thiol groups. Such sulfonic acid groups will also exchange with the silver, palladium or mercury when the thiol groups are exchanged. In some cases, the presence of exchanged sulfonic acid groups may be undesirable because the liquid carboxylic acid or anhydride being treated may contain metal ion impurities (e.g., sodium, iron, aluminum or calcium ions) in addition to iodide impurities. Such metal ion impurities can displace the silver, palladium or mercury bonded to the sulfonic groups. When the thiol resin has relatively few free thiol groups (e.g., when over 70% of 80% of the thiol groups have been exchanged with silver, palladium or mercury), such displacement decreases the amount of such metals available to remove the iodide impurities. On the other hand, when the resin has a relatively high proportion of free thiol groups, the free thiol groups can exchange with silver, palladium or mercury displaced from the sulfonic groups by the metal ion impurities and so the silver, palladium or mercury remains available to remove iodide impurities.

Further when the resin is washed with water after use to remove the acid or anhydride so as to render the spent resin safer to handle, the silver, palladium or mercury bonded to sulfonic groups can be displaced, especially if the water contains metal ion impurities.

On the other hand the silver, palladium and/or mercury bonded to thiol groups in the resins employed in the present invention are, because of the covalent nature of those bonds, less susceptible to displacement by metal ion impurities or by water washing than are silver, palladium or mercury ionically bonded to sulfonic groups.

Hence, in a preferred embodiment of this invention, any sulfonic acid groups in the thiol resins used as starting materials in producing the metal-exchanged resins used in the process of the invention are converted to less reactive groups by forming salts thereof (exchanged) with multivalent metals that have higher selectivity than silver, palladium or mercury for exchange with the sulfonic groups. Such conversion ("blocking" or "capping") can be achieved by reacting the sulfonic groups with a suitable metal salt (e.g., a calcium, aluminum or iron alkanoate) in a solvent for the salt at a temperature between the freezing point and the boiling point of the solvent (e.g., from 30° C. to 80° C.).

A suitable thiol resin useful as a starting material in producing the metal-exchanged resins used in the process of the present invention is Duolite® GT73 (previously sold as "IMAC TMR"). This resin is a macroporous ion exchange resin based on a crosslinked polystyrene matrix having greater than 90% of the functional groups as aryl thiol groups with a minor amount of the functional groups being sulfonic acid groups. Duolite® GT 73 contains 1.5 milliequivalents of thiol groups per milliliter of the resin. Another suitable resin starting material is Duolite® ES 465.

Prior to exchange with the metals, the total amount of thiol functional groups in the resins used in the process of this invention is usually from 1.2 to 1.8 equivalents per liter. The amount of silver, palladium and/or mercury present in the resins used in the process of the present invention is such that at least 1 percent and up to 100 of the functional groups initially in the resins have been exchanged by the metal. Preferably 30 to 70 percent of the thiol groups, more preferably 35 percent of the thiol groups, have been exchanged by the metal.

The metal-exchanged resins used in the process of the present invention can be prepared by ion-exchange (or impregnation) techniques known in the art. A preferred method for preparing silver-exchanged ("silver-loaded") resins is that described in above-mentioned published European Patent Application 296,584. This method involves slurrying the resin with silver oxide in water, adding acetic acid to form silver acetate, heating to produce the silver-exchanged resin and, if desired, washing the resin. A similar method may be used for preparing mercury-loaded resins from mercury (II) acetate. Palladium-loaded resins may be similarly prepared from palladium acetate but without the addition of water other than that used for washing the resin.

The process of the present invention may be carried out as a batch or continuous process and at any convenient pressure, subject to the acid or anhydride being a liquid under the conditions chosen.

The process of the present invention is suitably carried out by passing the carboxylic acid or carboxylic acid anhydride contaminated with iodide impurities (and possibly other impurities) through a fixed or moving bed of the resin at a predetermined rate. Preferably the resin bed is a fixed bed. The rate used will depend on a number of variables, including the amount of iodide impurities in the liquid carboxylic acid or carboxylic acid anhydride, the degree of purity required and the particular resin employed. Typical flow rates are in the range 0.5 to 30 (preferably 5 to 15) bed volumes per hour.

The temperature at which the process of the present invention is carried is not critical, although it must be high enough to prevent the liquid carboxylic acid or carboxylic acid anhydride from freezing at one extreme or boiling at the other. The temperature should also not be so high as to deactivate the resin (for example, exchanged Duolite® GT-73 may have a life of one year when used at 80° C.). Typical temperatures for carrying out the process of this invention are from 5° to 110° C. while preferred temperatures are from 25° to 80° C.

The process of the present invention is particularily suitable for removing iodide impurities from carboxylic acids having 2 to 6 carbon atoms inclusive and the corresponding anhydrides and mixed anhydrides, preferably acetic acid, propionic acid, acetic anhydride and propionic anhydride.

The process of the present invention is generally applicable to removing any iodide impurity from a carboxylic acid or anhydride. Such impurities include hydrogen iodide, alkyl iodides (particularly $C_1$ to $C_{10}$ alkyl iodides) and iodide salts.

After the metal-exchanged resin is used to remove iodide impurities in accordance with the process of this invention, it can be washed with water in order to remove the residual carboxylic acid or anhydride on the resin to make the spent resin safer to handle in metal reclamation. The washing can be accomplished simply by draining acetic acid from the bed and then flowing water through the bed until the acid or anhydride content of the spent resin has been lowered to the desired level. Metal exchanged thiol resins lose less of the exchanged metal than do metal exchanged sulfonic resins during iodide removal when other ionic impurities are also present and during washing with water containing ionic impurities after the resin is spent. Similarly, the capped and metal exchanged thiol resins used in a preferred embodiment of this invention lose less of the exchanged metal than uncapped metal-exchanged thiol resins during such use and washing when more (e.g., at least 75%) of the thiol groups have been exchanged with silver, palladium or mercury.

The present invention is illustrated by the following Examples.

EXAMPLE 1

Silver Exchanging of a Thiol Resin.

Two samples of Duolite® GT-73 were exchanged with silver using silver oxide as the silver source. In one experiment, 30% of the thiol groups in the sample were exchanged by silver and, in the other experiment, 50% of the thiol groups in the sample were exchanged with silver. The following procedure was followed: The resin was placed in a breaker and washed with water. The appropriate amount of silver oxide (i.e., 5.2 grams per 100 milliliters of resin for 30% exchange) was added to the beaker. Acetic acid was added to form silver acetate (50 to 60 grams) from the silver oxide (silver acetate is somewhat more soluble in the water than is silver oxide). The resulting mixture was heated to 50° C. for 2.5 hours. To determine if the silver was exchanged, a small amount of sodium chloride solution in water was added to about one milliliter of the liquid portion of the mixture. If silver is present, a white precipitate will be formed. Both resins took up all the silver as indicated by the sodium chloride test (i.e., no white precipitate formed). This test indicated that the resin readily reacted with and strongly bonded to the silver. These properties are necessary criteria for use in halide removal.

EXAMPLE 2

Batch Testing of an Exchanged Thiol Resin.

The following batch test is useful in screening metal-exchanged resins for their ability to remove iodides from acetic acid: 20 milliliters of metal-exchanged resins are placed in a beaker and rinsed with acetic acid. The acid is poured off and any residual acid is removed by suction through a glass capillary burette. 60 milliliters of acetic acid containing about 80 parts per billion of hexyl iodide and 20 parts per billion of methyl iodide are then poured into the beaker and mixed. Liquid samples are drawn off at intervals and analyzed for iodides.

Figure 1:
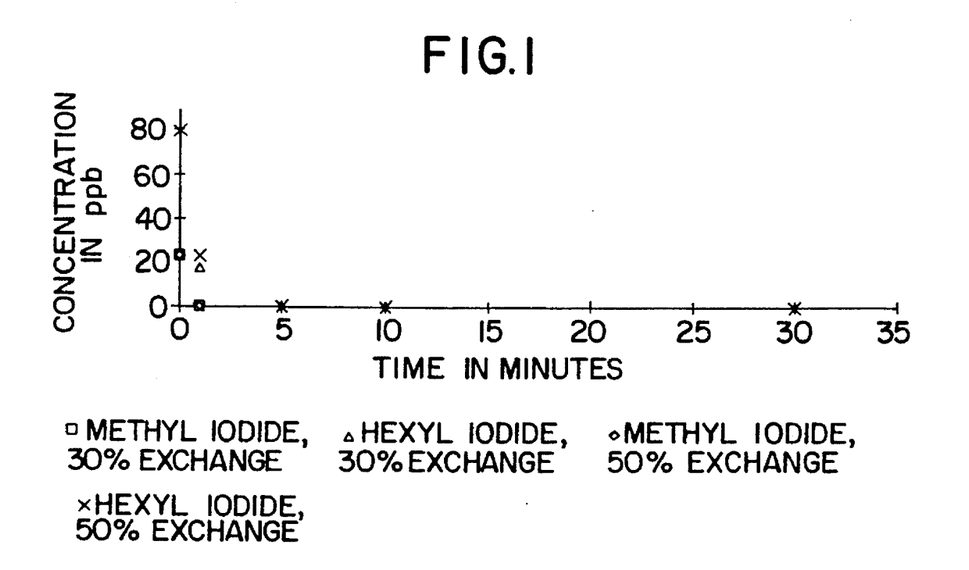
FIG. 1 shows the decrease in iodide impurities in acetic acid with time in two batch tests illustrating the practice of the present invention employing a silver-exchanged thiol resin.
Figure 2:
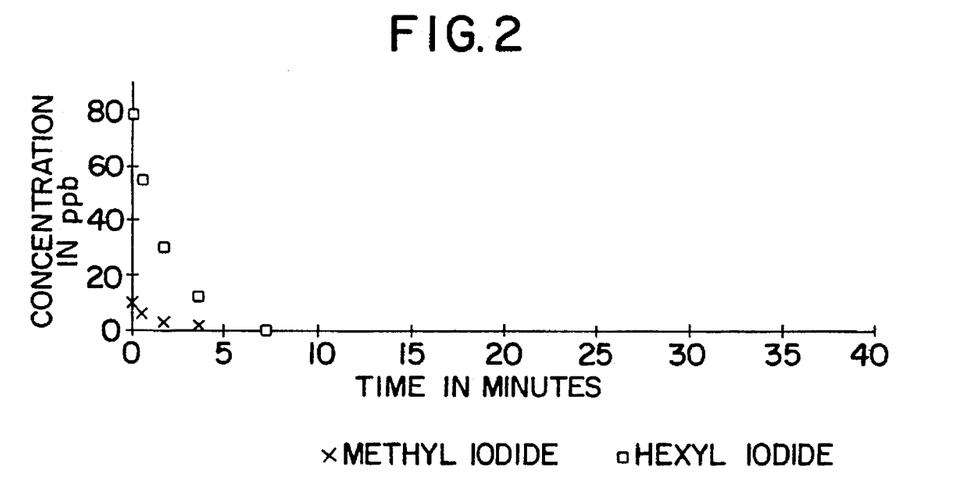
FIG. 2 shows the decrease in iodide impurities in acetic acid with time in a batch test illustrating the prior art employing a silver-exchanged sulfonic resin.

Two samples of Duolite® GT-73 in which 30% or 50% of the thiol groups had been silver-exchanged were tested by the above-described batch method. The results of the tests are given in FIG. 1. The higher silver loading did not have any measurable effect on the initial rate of iodide removal by this test. FIG. 2 shows comparative data taken on silver-exchanged Amberlyst® 15 (a sulfonic acid macroreticular resin). In all cases, the iodides are essentially removed in about 5 minutes. These results show that the performance of the thiol resin is comparable to the performance of silver-exchanged sulfonic acid macroreticular resin.

The data shown in FIG. 2 was obtained with 100 milliliters of acetic acid containing the iodide impurities to 20 milliliters of resin. The time axis has been corrected by multiplying the measured sample time by 60/100 to compare directly to FIG. 1. The data in FIG. 1, and all other batch testing described in the Examples herein, was obtained using 60 milliliters of acetic acid containing the iodide impurities to 20 milliliters of resin.

EXAMPLE 3

Determination of Sulfonic Acid Content of a Thiol Resin.

Duolite® GT-73 contains both thiol and sulfonic acid groups. Since sulfonic acid groups in resins are known to exchange with silver and to perform well in removing halide impurities, the concentration of sulfonic acid groups can influence resin performance and is desirably determined.

To determine the amount of sulfonic acid groups in Duolite® GT-73, that resin was washed in a column with excess aqueous $NaNO_3$. During the washing, the $Na^+$ ions exchanged with the $H^+$ ions of the sulfonic acid groups of the resin and nitric acid was formed. The thiol groups in the resin do not react with $NaNO_3$ under these conditions. The liquid from the washing contained the nitric acid and was titrated for acid content with methanolic potassium hydroxide. Phenolpthalein was used as the indicator. The milliequivalent of acid were calculated. The sulfonic acid concentration of the resin was found to be 0.256 milliequivalents per milliliter. Based on a total ion exchange capacity of 1.5 milliequivalents per milliliter (as reported by the manufacturer), the sulfonic acid groups made up 17% of the total functional groups in the resin.

EXAMPLE 4

Determination of Silver Distribution in an Exchanged Thiol Resin.

During the silver exchange of thiol resins containing both thiol and sulfonic acid functional groups, it is not known in the art which functional group the silver will attach to. If silver preferentially attaches to the thiol groups, the presence of the sulfonic acid groups may be insignificant with respect to iodide removal. On the other hand, if the silver attaches preferentially to the sulfonic acid groups, the thiol groups may not be responsible for the iodide removal.

Hence, a sample of 30% silver-exchanged Duolite® GT-73 resin was washed in a column with excess aqueous $NaNO_3$ and the liquid from the washing was titrated for acid content. The sulfonic acid concentration of the 30% silver-exchanged resin after $NaNO_3$ exchange was 0.184 milliequivalents per milliliter. About 16% of the silver was exchanged on the sulfonic acid groups. This indicates that the silver does not preferentially exchange with either group.

EXAMPLE 5

Calcium Blocking of Sulfonic Acid Groups in a Thiol Resin.

To determine if the thiol groups in ion exchange resins are active for iodide removal, Duolite® GT-73 was treated with $Ca^{2+}$ to "block" (i.e., to react to form a stable salt) the sulfonic acid groups. Calcium acetate was used as the calcium source. Blocking was accomplished by dissolving 24 grams of calcium acetate in 500 milliliters of water and mixing the solution so formed with 100 milliliters of the resin. The mixture was maintained at 50° C. for 2 hours.

After blocking the sulfonic acid groups with calcium as described above, the resin was exchanged with silver (in the form of silver acetate) in the presence of excess $Ca^{2+}$ (in the form of aqueous calcium acetate) to produce a resin in which 30% of the thiol functional groups were occupied by silver.

Using the procedure described above, calcium blocking and silver exchange were also performed on Amberlyst® 15 (a strong acid macroreticular ion exchange resin) as a control. If all the silver had been taken up by the resin, a 25% silver loaded resin would have been produced because of the high capacity of the Amberlyst® 15 resin.

The silver was taken up rapidly by the thiol resin as indicated by the NaCl test (see Example 1 above) after 15 minutes. Silver testing of the Amberlyst® 15 resin was strongly positive (a copious white precipitate formed) after one hour, indicating that only a portion, if any, of the silver was taken up by the resin. These results indicate that the calcium blocking procedure prevents silver from attaching readily to the sulfonic acid groups.

EXAMPLE 6

Figure 3:
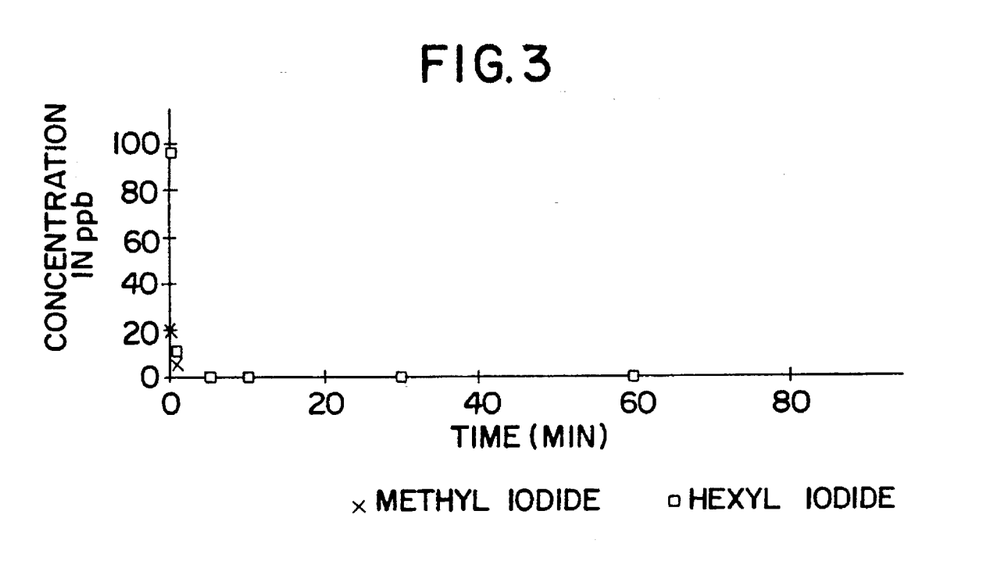
FIG. 3 shows the decrease in the iodide impurities with time in a batch test illustrating the practice of the present invention employing a silver-exchanged and calcium capped thiol resin.
Figure 4:
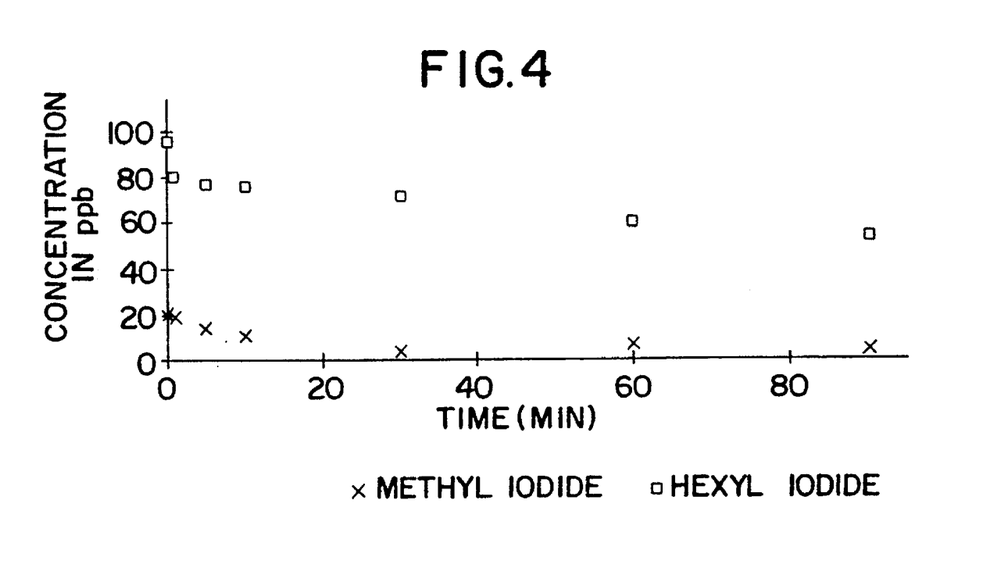
FIG. 4 shows the small decrease in the iodide impurities with time in a batch test employing a sulfonic resin capped with calcium.

Batch Testing of Calcium Blocked and Metal-Exchanged Thiol and Sulfonic Acid Resins Duolite® GT-73 and Amberlyst® 15, which had been $Ca^{2+}$ blocked and silver-exchanged as described in Example 5 above, were tested for ability to remove iodide impurities by the batch screening method described in Example 2 above and the results as shown in FIGS. 3 (for Duolite® GT-73) and FIG. 4 (for Amberlyst® 15).

As shown in FIGS. 3 and 4, the performance of the thiol resin (Duolite® GT-73) was not altered by the calcium blocking procedure but the performance of the sulfonic acid resin (Amberlyst® 15) was dramatically reduced. Even after 100 minutes, only very slight removal of iodide impurities was achieved by the Amberlyst® 15.

Figure 5:
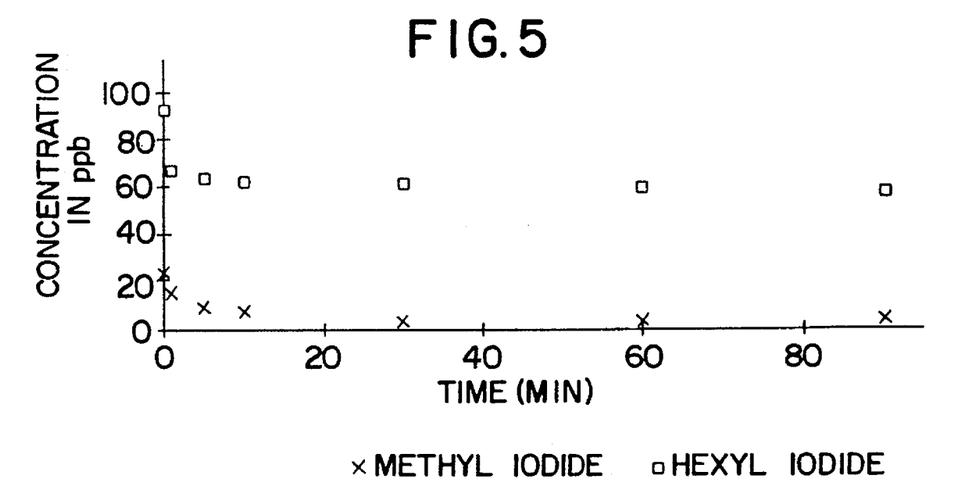
FIG. 5 shows the decrease in the iodide impurities with time in a batch test illustrating the prior art employing a sulfonic resin at 1% silver loading.
Figure 6:
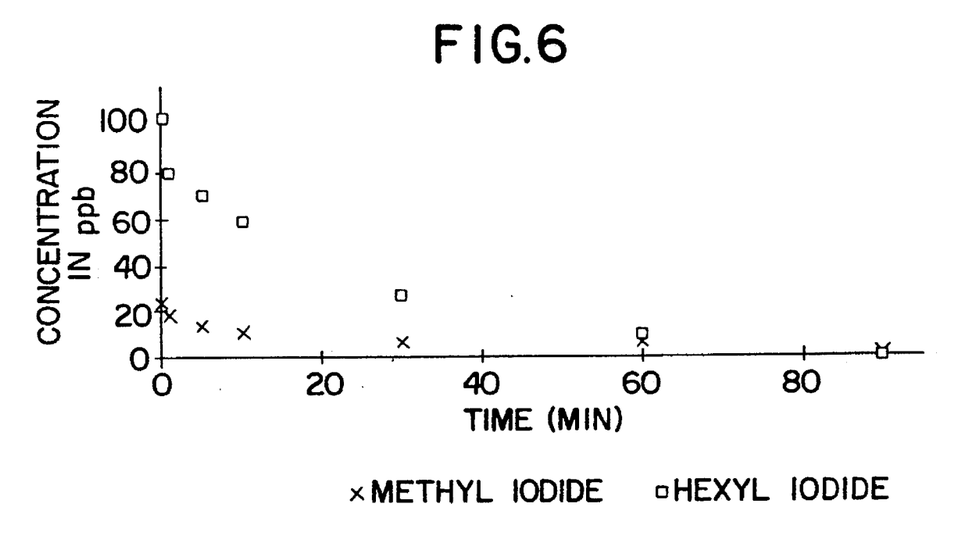
FIG. 6 shows the decrease in the iodide impurities with time in a batch test illustrating the prior art employing a sulfonic resin at 5% silver loading.

Amberlyst® 15 was silver exchanged at levels of 5% and 1% and batch tested. These results are shown in FIGS. 5 and 6. The 5% silver-exchanged resin performed substantially better than the $Ca^{2+}$ blocked resin which had been treated with sufficient silver to have resulted in a 25% silver exchange if the silver had completely exchanged with the resin. The performance of the 1% exchanged resin is comparable to the $Ca^{2+}$ treated resin shown in FIG. 4. These results confirm that calcium blocking does occur with most of the sulfonic acid groups and so prevents them from exchanging with silver. These results also confirm that the exchanged thiol groups on the Duolite® GT-73 resin are responsible for the good performance of the resin, even when the sulfonic acid groups are blocked.

EXAMPLE 7

Silver Impregnation of Various Weak Acid Exchange Resins.

Four weak acid ion exchange resins were treated by the silver exchange process described in Example 1 above to determine if they would readily exchange and hold the silver. The resins tested were IRC 76, a resin contains carboxylic acid groups and which is sold by Rohm and Haas Company, Amberlite® IRC 718 (a chelating resin containing iminodiacetic acid functional groups sold by the Rohm and Haas Company), LEWATIT® TP 214 (a chelating resin containing thioureido functional groups sold by Bayer AG) and LEWATIT® Vers Prod OC 1060 MD (a resin containing aminophosphonic acid functional groups sold by Bayer AG).

These resins were all exchanged by the same procedure using the same amount of silver for a given volume of resin in each case. The silver loading was a nominal 30% capacity based on a resin capacity of 1.5 milliequivalents per milliliter. The actual capacity varied somewhat due to the slightly different capacities of the resins.

The only resin from this group which readily took up the silver was the LEWATIT® TP 214. The liquid from the other resins all tested positive for silver at the end of the impregnation step. These results indicate that weak acid resins do not, in general, exchange readily with silver.

EXAMPLE 8

Testing of Weak Acid Ion Exchange Resins.

Figure 7:
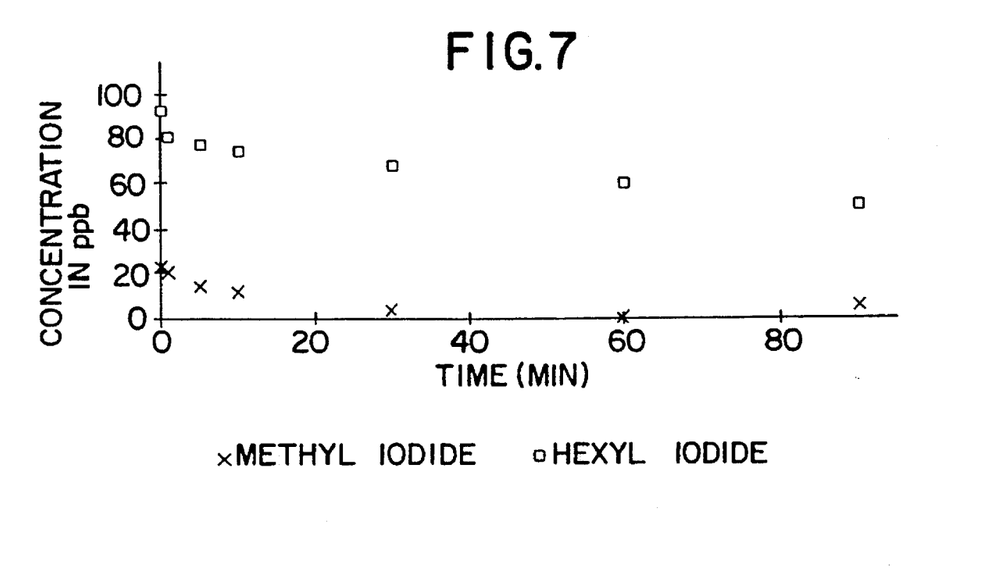
FIG. 7 shows the decrease in the iodide impurities with time in a batch test illustrating a weak acid ion exchange resin.

The resins prepared in Example 7 above were tested for iodide removal by the batch test method described in Example 2 above. All resins showed substantial silver loss during the test, except for LEWATIT® TP 214. Such silver loss is unacceptable in most applications as it will result in poor product quality and increased deactivation rate of the resin. The performance of the LEWATIT® TP 214 is shown in FIG. 7. Although this resin did hold silver, it did not perform well in hexyl iodide removal and its performance was similar to a 1% silver-exchanged prior art Amberlyst® 15 resin.

EXAMPLE 9

Effect of $Ca^{2+}$ Cation in Acetic Acid Feed on Silver Loss.

Two resins were tested for their ability to hold the silver when with 0.16 wt.% calcium acetate in acetic acid. The resins tested were the Duolite GT-73 (a thiol resin) exchanged at 15% and Amberlyst® 15 (a sulfonic acid resin) exchanged at about 30%.

20 cubic centimeters of each resin was packed in a column and the acetic acid solution was passed through the column at a rate of about 5 cubic centimeters per minute and at room temperature. The liquid effluent from the column was collected in increments of about 30 bed volumes and analyzed for silver.

Initially, both resins held the silver well. That is, the detection limit of the silver analysis method used was about one part per million and the initial effluents from both columns had about that amount of silver.

Figure 8:
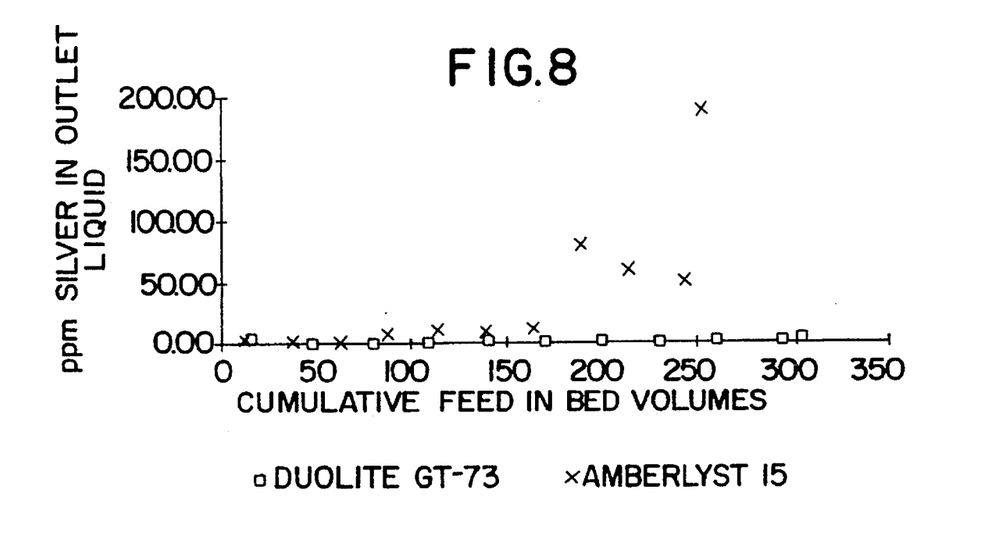
FIG. 8 shows the effect of capping on the silver loss of a silver-exchanged thiol resin and a silver exchanged sulfonic resin when washed with acetic acid containing calcium ions as an impurity.

However, the sulfonic acid resin began to lose silver as the test proceeded as shown in FIG. 8. The calcium apparently initially exchanges with the unexchanged sulfonic acid groups on the resin but later begins to exchange with the groups exchanged with silver. The silver concentration in the outlet liquid increased to 80 parts per million in the case of the Amberlyst® 15. Then, the silver loss began to taper off.

The Duolite GT-73 did not show any increase in silver loss. Apparently, any silver displaced from the sulfonic groups in Duolite GT-73 by calcium exchanged with some of the excess free thiol groups and so there was no increase in silver loss. At the end of the tests, each resin was washed with ten bed volumes of water and the resulting wash water was analyzed for silver. When the silver exchanges with the calcium, the resulting product is silver acetate, which has limited solubility in acetic acid, but greater solubility in water. The last data point for each resin in FIG. 8 was taken from the water washing step. The silver-exchanged sulfonic acid resin showed substantial loss of silver while the silver-exchanged thiol resin did not show substantial loss of silver. The silver concentration from the Amberlyst® 15 wash water was 190 parts per million while the silver concentration from the Duolite® GT-73 wash water was less than 4 parts per million. The upper permissible concentration of silver from an environmental standpoint is 5 parts per million.

EXAMPLE 10

Life Testing on Thiol Resin at Ambient Temperature and 50° C.

Figure 9:
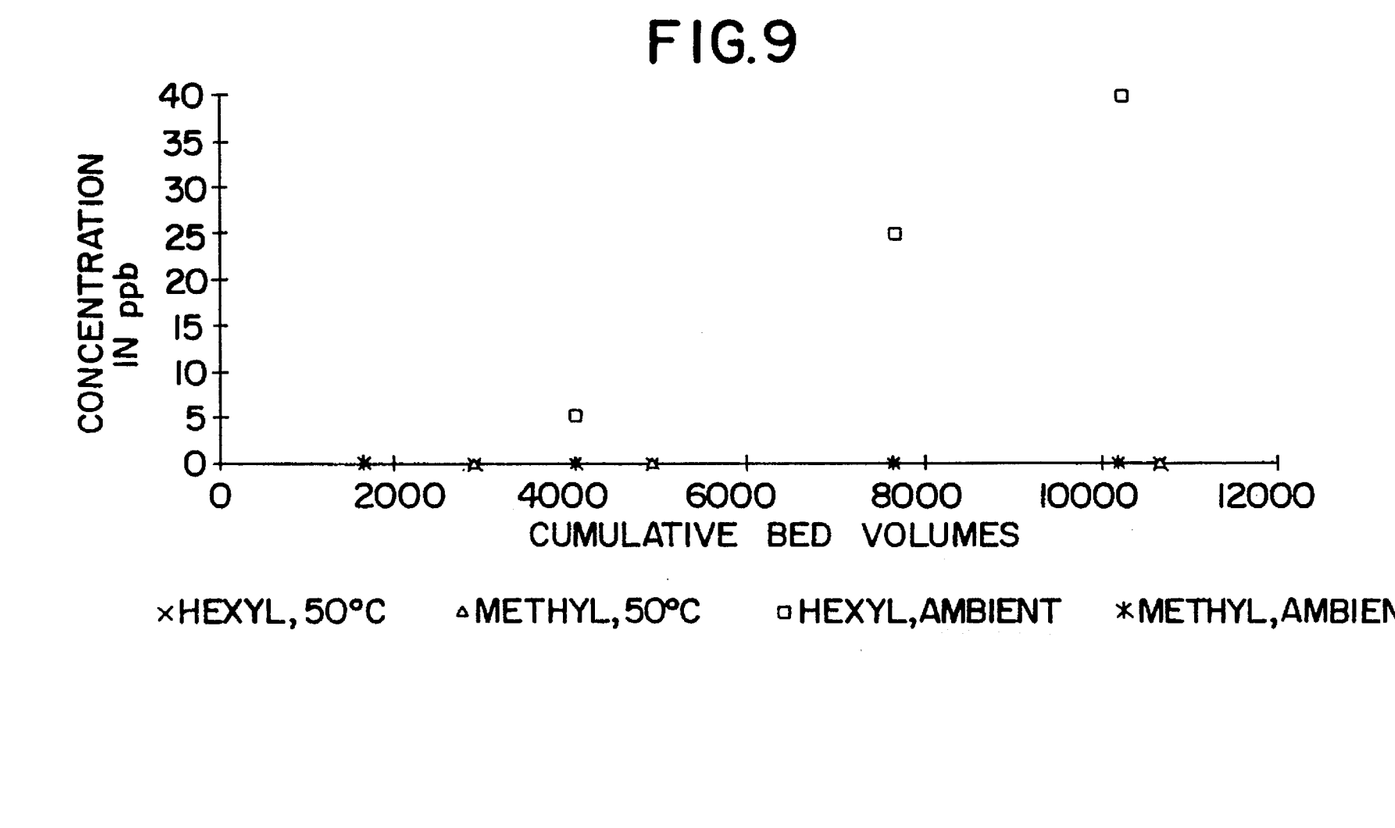
FIG. 9 shows the effect of temperature on the ability of silver exchanged thiol resin to remove iodides.

Duolite® GT-73, 30% silver exchanged, was tested for its ability to remove iodides at ambient temperature (about 22° C.) and at 50° C. The feed rate to the resin bed was held at about 0.25 bed volumes/minute in both cases over the duration of the life test. The feed contained 80 parts per billion of hexyl iodide and 20 parts per billion of methyl iodide in acetic acid. FIG. 9 shows the results of outlet iodide concentration versus cumulative bed volumes of acetic acid feed passed through the bed. Initially, both beds removed all of the iodides fed. However, the hexyl iodide was seen in the outlet at 4000 bed volumes in the column performing at ambient temperature, and the outlet increased to about 40 parts per billion by 100,000 bed volumes. No methyl iodide was seen in the outlet in either case. No break through of hexyl iodide was seen on the column operating at 50° C. during the time of the testing. The data shows that the life of the resin is improved as the operation temperature is increased. The upper temperature limit is determined by the temperature stability of the resin and by the extent to which the degradation by products of the resin can be tolerated (e.g., the extent to which sulfur-containing degradation by products can be tolerated in the acid or anhydride from which the iodide impurities are being removed).

What is claimed is:

1. A composition of matter comprising an ion exchange resin: (a) containing from 0.1 to 2.5 milliequivalents of thiol groups per milliliter of resin wherein over 75% of the thiol groups have been exchanged with silver, palladium or mercury; and (b) wherein from 1% to 20% of the functional groups in the resin are sulfonic acid groups reacted with calcium, aluminum or iron.

* * * * *